United States Patent [19]

Simmons

[11] Patent Number: 5,597,303

[45] Date of Patent: Jan. 28, 1997

[54] DEVICE AND METHOD FOR CONFIRMING BITE REGISTRATION FOR DENTAL IMPLANTS

[76] Inventor: David E. Simmons, 1534 Aline St., New Orleans, La. 70115

[21] Appl. No.: 390,079

[22] Filed: Feb. 17, 1995

[51] Int. Cl.⁶ .................................................. A61C 19/04
[52] U.S. Cl. .................................................. 433/74; 433/69
[58] Field of Search ............................... 433/68, 69, 70, 433/71, 74

[56] References Cited

U.S. PATENT DOCUMENTS

| | | | |
|---|---|---|---|
| 2,389,063 | 11/1945 | Lang | 433/69 |
| 2,507,118 | 5/1950 | Opstow | 433/69 |
| 2,552,829 | 5/1951 | Wilkinson | 433/68 |
| 2,674,798 | 4/1954 | Craigo | 433/71 |
| 2,792,629 | 5/1957 | Green | 433/69 |
| 3,686,761 | 8/1972 | Gravon | 433/71 |
| 4,332,556 | 6/1982 | Daiberl | 433/69 |
| 4,432,728 | 2/1984 | Skarky | 433/71 |
| 4,472,140 | 9/1984 | Lustig | 433/71 |
| 4,543,062 | 9/1985 | Lee | 433/71 |

FOREIGN PATENT DOCUMENTS

| | | | |
|---|---|---|---|
| 3640524 | 6/1988 | Germany | 433/71 |

*Primary Examiner*—Paul J. Hirsch
*Attorney, Agent, or Firm*—Keaty & Keaty

[57] ABSTRACT

The invention relates to a device and method for confirming bite registration for dental implants. The device has an elongated plate having one or more openings formed at an angle to a longitudinal axis of the plate. A hollow post has an exterior wall corresponding in size and shape to the openings in the plate so as to fittingly slide through a selected plate opening. An inner aperture in the post is suitable for engaging with a portion of the dental implant that extends above the healed gumline of a patient. When the post is engaged with the implant, and the plate is placed over the post, an outer surface of the plate is oriented in a substantially parallel relationship to an occlusal plane. The post and the plate are secured together to register orientation of the dental implant in relation to the occlusal plane.

15 Claims, 2 Drawing Sheets

DEVICE AND METHOD FOR CONFIRMING BITE REGISTRATION FOR DENTAL IMPLANTS

BACKGROUND OF THE INVENTION

This invention relates to a device for establishing an accurate bite between the upper and lower teeth after a "root form" implant has been surgically installed in the upper or lower jaw. A conventional technique for positioning implants comprises a step of securing a fixture, which can be threaded or non-threaded, into the jaw bone and leaving it there for a discreet period of time to allow a healing process to take effect, so that the bone becomes biologically attached to the fixture.

The fixture usually comprises a hollow cylinder, the outer and inner curved surfaces of which are provided with threads. It is strategically positioned in such a way that the upper end surface is located at the same level as the surface of the jawbone. During a second step, the healed membrane is cut to expose the upper end surface of the fixture, and a spacer is screwed into the center aperture of the implanted fixture. This fixture will serve as an ultimate attachment of a prosthetic tooth to the anchor.

In order to fabricate a prosthesis over the implants a master model of the patients mouth must be made. One method is to make a replica of each implant an its relationship to any remaining teeth in master model. The other method is to attache a restorative abutment to each implant and make a replica of the relationship of these abutments in a master model.

To make a master model an impression post must be secured to each implant (If the abutments are in place an impression post is secured to each abutment). A standard dental impression is taken with an impression tray and a material such as rubber. When this impression is removed from the mouth, the impression posts are retained in the impression. A replica of the implant or abutment (lab analog) is attached to each impression post that has been retained in the impression. Dental stone is now poured into the impression to make a master model.

At this stage relating this master model accurately to a model of the opposite jaw in the laboratory is difficult without many teeth present in the area of the implants. This usually requires the patient to return to the office for one or more appointments before the prosthesis can be completed. If the initial impression is not accurate, the support structure is cut and reassembled. In some cases, the impression of the patients mouth has to be taken again in an attempt to replicate the relationship of the implants.

The present invention contemplates provision of an implant registration system which can be used to check the accuracy of duplication of the relationship of the implants to each other and the remaining teeth.

SUMMARY OF THE INVENTION

It is, therefore, an object of the present invention to provide a system that attaches to the implants to create a custom "bite table". This can be used to record the relationship of the lower jaw to the upper jaw.

It is a further object of the present invention to provide a system which can be used to check the accuracy of the master model.

It is a further object of the present invention to provide a system which is easy to use and inexpensive to manufacture.

These and other objects of the present invention are achieved through a provision of a device for confirming bite registration for dental implants which comprises an elongated plate having at least one opening therein, with the opening defined by an annular wall which is oriented at an angle to correspond to the angle of natural position of a implant in the patient's mouth. A hollow post which has an exterior surface sized and shaped to correspond and fittingly engage through the plate opening is formed with an inner aperture suitable to fittingly engage a portion of the dental implant or abutment which extends through a healed gumline. The post is positioned over that portion of the implant which is exposed through the gumline, and the plate with the properly oriented opening is fittingly engaged by slipping it over the post. A part of the post is severed, such that the outer part of the post is at a level below the upper edge of the adjacent teeth, while the plate is oriented in a substantially parallel relationship to the occlusal plane. This plate must orient below the occlusal plane to allow space for a bite registration material.

The plate is then also severed to the appropriate length so that when in place it will approximate the remaining teeth or other posts with plates attached. The post and the plate are secured together and secured to any adjacent posts and plates, thereby registering orientation of the dental implant or implant with abutment in relationship to the occlusal plane.

If desired, the bite registration is placed over the outer surface of the plate and the opposite teeth of the patient are brought into engagement with the bite registration material until that material hardens, leaving an accurate imprint of the orientation of the dental implant and jaw in relationship to the opposing teeth.

In an alternative embodiment, the plate can be made with a plurality of openings, with each opening oriented at a different angle, allowing a doctor to select that particular part of the plate for engagement with the post which most closely approximates the orientation of the implant in relation to the occlusal plane. In this embodiment, a portion of the post extending outwardly from the outer surface of the plate is also severed, so as to retain the outer surface of the plate at a level below the edges of the adjoining teeth.

BRIEF DESCRIPTION OF THE DRAWINGS

Reference will now be made to the drawings, wherein like parts are designated by like numerals, and wherein.

DETAIL DESCRIPTION OF THE PREFERRED EMBODIMENT

Figure 1:
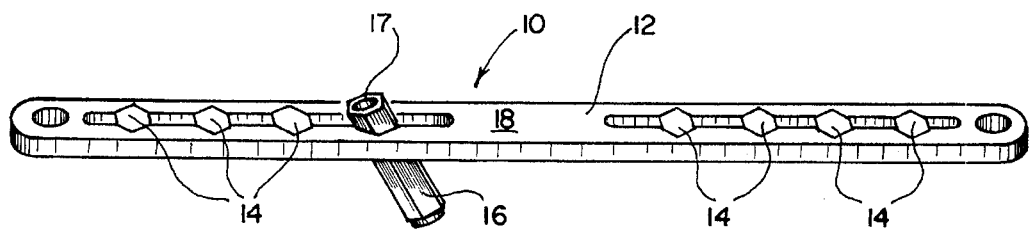
FIG. 1 illustrates a bite table plate in accordance with the present invention along with a post positioned in one of the openings in the plate.

Referring now to the drawings in more detail, numeral 10 designates a bite registration device in accordance with the present invention. The device 10 comprises an elongated plate 12 having one or more apertures 14 formed in a spaced-apart relationship. The apertures 14 are formed at an angle to a longitudinal axis of the plate 12, with each aperture being formed at a different angle.

Figure 2:
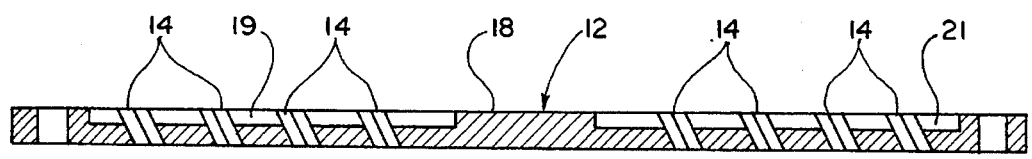
FIG. 2 illustrates a cross-sectional view showing a bite table plate formed with a plurality of angularly disposed openings.

The angle of the aperture which passes through the thickness of the plate 12 can be 5 degrees–90 degrees in relationship to flat surfaces defining the outer and inner surfaces of the plate 12. The angles may also be described as being at a selected angular position to an imaginary line which is perpendicular to the occlusal plane that is assumed to be 0 degrees. FIG. 2 shows, in a cross-sectional view, a relative orientation of a plurality of openings 14 formed in the plate 12. As can be seen in the drawing, each of the openings 14 is oriented at a slightly different angle from all other openings 14 made in the plate 12. This variance in angular position will allow a doctor to select the angle most closely approximating the orientation of an implant exposed through the gumline. As can be further seen in FIGS. 1 and 2, the plate 12 is formed with a pair of elongated groove 19 and 21 extending in the outer surface 18 of the plate 12. The openings 14 have greater diameter than the groove 19 and 21, as can be seen in FIG. 1, allowing the doctor to facilitate easy positioning of a post 16 within one of the preselected openings 14. The openings 14 are defined by hexagonally shaped interior wall which is adapted to receive in a fittingly close relationship a support abutment post which has hexagonal exterior wall sized and shaped to precisely fit within one of the openings 14. The post 16 has an inner aperture 17 which extends through the length of the post. The size and shape of the aperture allows to fit the post and secure the post 16 to an implant.

The device of the present invention is designed with the recognition of the fact that the implants are not usually placed at a strictly perpendicular angle to the occlusal plane. The design of the present invention allows to provide bite registration and receive precise impression of the natural position of the implant extending through the gum line.

The next step in the process of preparing a suitable bite table is selecting the correct angle at which the implant extends and positioning a support abutment post 16 over the implant portion which is exposed through the gumline 15. Each abutment post 16 is internally shaped and sized to fit precisely to the implant. The opening which extends in the post 16 corresponds to an external shape of an implant, for example an external hexagonal shape of a branemark implant. The plate 12 is then slipped over the post 16 such that the post extends through a properly angularly oriented opening 14. The plate 12 is then severed into segments, such that a portion of the plate which surrounds the selected opening 14 is retained in a fitting engagement with the post.

Figure 3:
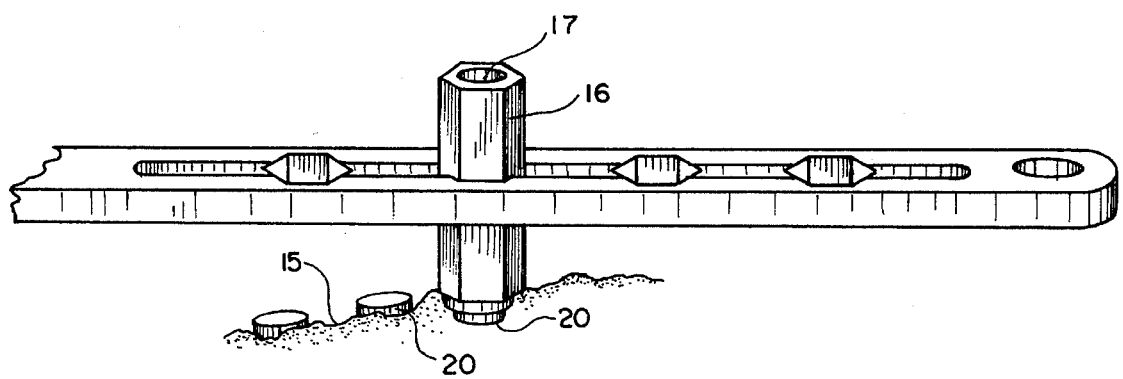
FIG. 3 illustrates the bite table plate and a post secured to the implant.

The plate 12 has preferably more than one opening 14, each opening being oriented at a different angle to allow selection of the necessary angle of the opening depending on the orientation of the exposed implant. Since each implant is usually oriented at a different angle, the selected opening will be different to allow creation of a properly angled bite table. If more than one implant 20 is involved, the plate is severed into a number of individual segments 22, allowing posts 16 to be surrounded by a straight outer surface 18 of the plate segments 22, as shown in FIG. 3.

Even though this description and the drawings describe and illustrate the present invention in use with implants in the lower jaw, it will be apparent to those skilled in the art that it can be equally adapted for use with the upper jaw implants.

The outer surface 18 is located below the edge of natural teeth, or other prosthesis, 21 which is present in the mouth of the patient. As can be seen in FIG. 3, the outer surface 18 is substantially parallel to the occlusal bite plane which insures that a proper bite alignment can be made with the help of the plate 12. The posts 16 are then cut to the proper height to slightly extend outwardly from the outer surface 18, and the posts 16 are attached to the implants. If more than one implant is involved, the individual segments 22 of the plate 12 are rotated to be closely positioned to each other.

The next step in the process involves placing a resinous moldable material between the individual segments 22 and allowing the moldable material to harden thereby attaching the segments 22 to each other and to the posts 16 so as to form a unit.

Once the material hardens, a bite registration material is placed over the created unit in the amount sufficient to allow the upper teeth 24 to meet with the registration material and form an impression of the accurate bite.

Figure 4:
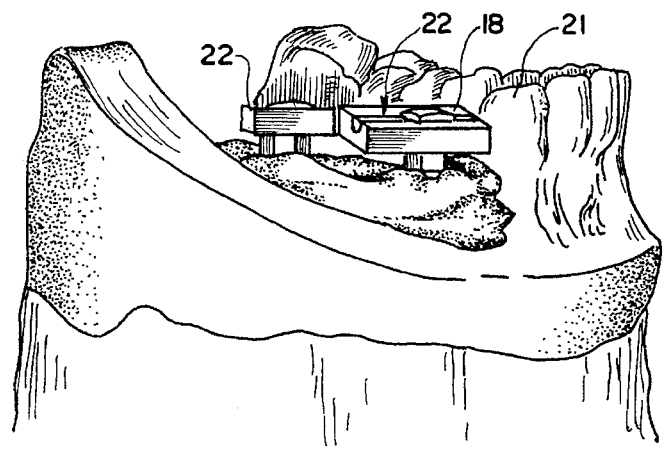
FIG. 4 illustrates the bite table plate divided into a number of segments with the posts cut to a desired height and retained on the implants.

FIG. 4 illustrates this step of the process, wherein two segments 22 of the plate 12 are shown joined by a securing material 26 such that the top surface 18 of the segments 22 is substantially parallel to the occlusal plane.

The bite registration material, which can be a bite registration paste or wax, is designated by numeral 28 in FIG. 4. The bite registration material 28 is soft enough in the beginning to receive the impression of the upper teeth 24 of the patient. The patient is then guided to close the mouth in a centric relationship, leaving a permanent imprint on the registration material 28 which can be used for subsequent verification of the implant accuracy.

Once the registration material 28 hardens, it is removed and saved. The screws which are placed in the implant are removed, allowing to lift the entire table comprised of the glued together segments 22 and the posts 16 from the implants.

Figure 5:
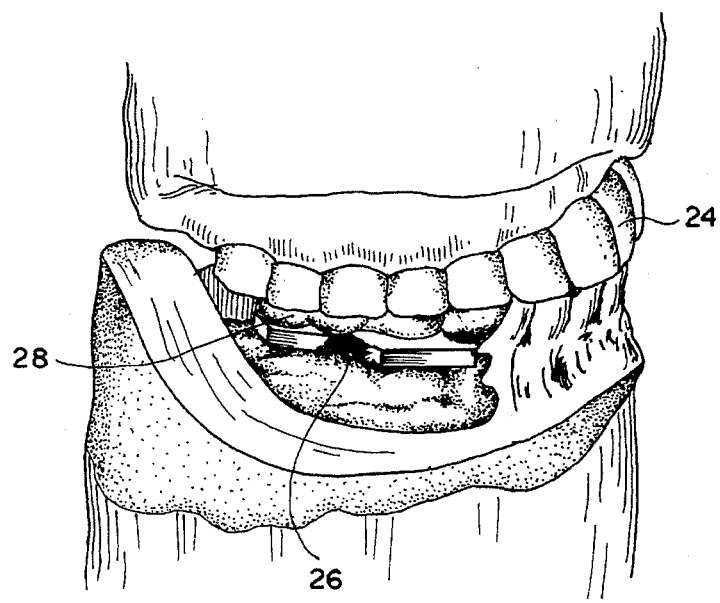
FIG. 5 is a schematic view illustrating implant verification, with the mouth closed, and the bite registration material in place.
Figure 6:
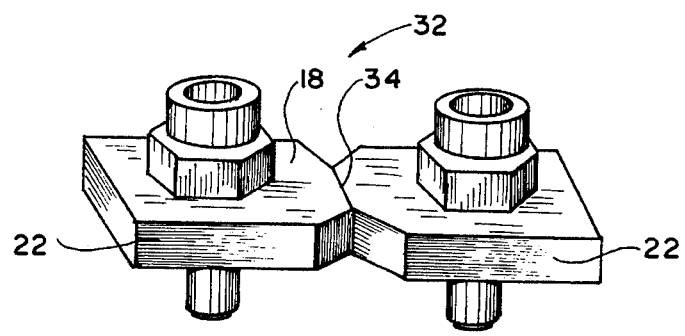
FIG. 6 is schematic view illustrating the bite registration impression verification assembly removed from the mouth as a unit.

FIG. 5 illustrates a view of the verification table 32 which is composed of two adjacent segments 22 joined together at the adjacent surfaces 34. The screws of the implants, as well as the posts 16 remain attached to the table 32.

When the master working model is completed in a laboratory, the bite verification table 32 is secured down to fit exactly as it fit on the patient during the steps described previously. If the fit is accurate, the technician carries the prothesis to completion without the need for a further fitting appointment with the patient. If the table 32 does not fit the master model, the support structure will have to be fitted before the prosthesis is completed.

The present invention eliminates the need for the patient to come for one or more appointments since the verification of the relationship of the implants to each other and to the upper or lower teeth present in the patient's mouth can be done at the same time as the bite registration. Consequently, the cost of the implant procedure is substantially reduced and discomfort to a patient during an extra fitting appointments is eliminated.

Many changes and modifications can be made in the device and method of the present invention without departing from the spirit thereof. I, therefore, pray that my rights to the present invention be limited only by the scope of the appended claims.

I claim:

1. A device for confirming bite registration for dental implants, comprising:

a substantially flat plate of a discreet length having an outer surface, an inner surface and a through opening, said opening being defined by an annular wall oriented at an angle which generally corresponds to an angle of natural position of a healed dental implant extending above a patient's gumline; and a hollow post having a first portion for engaging said dental implant, said first portion extending outwardly from said inner surface, a second portion which extends outwardly from said outer surface after the post has been fittingly engaged in said through opening, said post being provided with an inner aperture suitable to fittingly engage the portion of the dental implant extending above a patient's gumline.

2. The device of claim 1, wherein said plate outer surface extends in a substantially parallel relationship to an occlusal plane when said plate is positioned in a frictional engagement over said post after the post has been fitted over a portion of the dental implant.

3. The device of claim 1, wherein said plate opening has a hexagonal cross section and the exterior wall of said post is shaped to correspond to the plate opening.

4. The device of claim 2, wherein said post extends at an angle to an occlusal plane when said post is engaged with said plate.

5. A device for confirming bite registration for dental implants, comprising:

a substantially flat plate of a discreet length having an outer surface, an inner surface and a plurality of through openings, each of said openings being defined by an annular wall oriented at an angle which is selected to generally correspond to an angle of natural position of an individual healed dental implant extending above a patient's gumline; and a hollow post having a first portion for engaging said dental implant, said first portion extending outwardly from said inner surface and, a second portion which extends outwardly from said outer surface after the post has been fittingly engaged in a selected through opening, said post being provided with an inner aperture suitable to fittingly engage the portion of the dental implant extending above the patient's gumline.

6. The device of claim 5, wherein said plate outer surface extends in a substantially parallel relationship to occlusal plane when at least a portion of said plate is positioned in a frictional engagement over said post after the post has been fitted over a portion of a selected dental implant.

7. A method of confirming bite registration for dental implants, comprising the steps of:

providing a plate having a discreet length and at least one opening extending through said plate at an angle to a longitudinal axis of the plate;

providing a hollow post having an exterior wall sized and shaped to fittingly extend through the plate opening, said post being provided with an aperture defined by an annular wall to fittingly engage at least a portion of a dental implant extending above a patient's gumline;

positioning said post in a secure engagement with said portion of the dental implant;

placing the plate over said post such that an outer surface of the plate is oriented in a substantially parallel relationship to an occlusal plane;

securing said post to said plate, thereby registering orientation of the dental implant in relationship to the occlusal plane.

8. The method of claim 7, further comprising a step of placing a moldable bite registration material over said outer surface and engaging said registration material with opposing teeth of the patient so as to receive an accurate imprint of orientation of the dental implant in relationship to the opposing teeth.

9. The method of claim 7, wherein said plate opening has hexagonal cross section, and an exterior wall of said post is sized and shaped to correspond to the plate opening.

10. The method of claim 7, wherein said post extends at an angle to the occlusal plane when said post is engaged with said plate.

11. The method of claim 7, wherein said plate opening is selected to generally correspond to an angle of natural position of a healed dental implant.

12. The method of claim 7, further comprising a step of severing a portion of said post which extends outwardly from the outer surface of said plate prior to securing said post to said plate.

13. A method of confirming bite registration for dental implants, comprising the steps of:

providing a plate having a discreet length and a plurality of openings, each of said openings extending at a different angle in relation to a longitudinal axis of the plate;

providing a hollow post having an exterior wall sized and shaped to fittingly extend through said plate opening and an aperture defined by an annular wall adapted to fittingly engage at least a portion of a dental implant extending above a patient's gumline;

positioning said post in a secure engagement with said portion of the dental implants;

selecting an opening in the plate the angular orientation of which corresponds to an angle of a healed natural orientation of a healed dental implant;

severing the plate at diametrically opposite locations adjacent said opening, while retaining a part of the plate adjacent said opening;

placing the plate over said post such that selected angle of the plate opening corresponds to an angle of protrusion of the dental implant over a healed gumline, while an outer surface of the plate is oriented in a substantially parallel relationship to an occlusal plane; and securing said post to said plate, thereby registering orientation of the dental implant in relationship to the occlusal plane.

14. The method of claim 13, further comprising a step of placing a moldable bite registration material over said outer surface and engaging said registration material with opposing teeth of the patient, so as to receive an accurate imprint of the orientation of the dental implant in relation to the opposing teeth.

15. The method of claim 13, further comprising a step of severing a portion of the post which extends outwardly from the outer surface of the plate prior to securing said post to said plate.

* * * * *